United States Patent
Lallemand et al.

(10) Patent No.: US 9,616,016 B2
(45) Date of Patent: Apr. 11, 2017

(54) METHOD FOR TREATING RETINAL CONDITIONS USING AN INTRAOCULAR TAMPONADE

(75) Inventors: Frédéric Lallemand, Fresnes (FR); Jean-Sébastien Garrigue, Verrieres-le-Buisson (FR); Jeffrey Heier, Boston, MA (US)

(73) Assignee: SANTEN SAS, Evry (FR)

( * ) Notice: Subject to any disclaimer, the term of this patent is extended or adjusted under 35 U.S.C. 154(b) by 179 days.

(21) Appl. No.: 12/950,063

(22) Filed: Nov. 19, 2010

(65) Prior Publication Data

US 2011/0124616 A1    May 26, 2011

Related U.S. Application Data

(60) Provisional application No. 61/262,719, filed on Nov. 19, 2009.

(30) Foreign Application Priority Data

May 28, 2010 (EP) .................................. 10164362

(51) Int. Cl.
*A61K 31/573* (2006.01)
*A61K 9/00* (2006.01)
*A61K 47/14* (2017.01)

(52) U.S. Cl.
CPC .......... *A61K 9/0048* (2013.01); *A61K 9/0051* (2013.01); *A61K 47/14* (2013.01)

(58) Field of Classification Search
CPC ..... A61K 9/0051; A61K 47/14; A61K 9/0048
See application file for complete search history.

(56) References Cited

U.S. PATENT DOCUMENTS

| | | | | |
|---|---|---|---|---|
| 4,716,154 A | * | 12/1987 | Malson et al. ................... | 514/54 |
| 5,441,733 A | * | 8/1995 | Meinert ...................... | 424/78.04 |
| 5,698,219 A | * | 12/1997 | Valdivia et al. .............. | 424/450 |
| 2004/0071751 A1 | | 4/2004 | Maki et al. | |
| 2004/0147599 A1 | | 7/2004 | Gagnon et al. | |
| 2004/0197340 A1 | | 10/2004 | Luyckx et al. | |
| 2006/0233859 A1 | * | 10/2006 | Whitcup et al. .............. | 424/427 |
| 2007/0203173 A1 | * | 8/2007 | Mudumba ............ | A61K 31/445 514/291 |
| 2007/0218007 A1 | | 9/2007 | Chang et al. | |
| 2008/0181867 A1 | | 7/2008 | Lambert et al. | |
| 2012/0238536 A1 | | 9/2012 | Garrigue et al. | |

FOREIGN PATENT DOCUMENTS

| | | | |
|---|---|---|---|
| CN | 101062040 A | 10/2007 | |
| WO | 9921512 A1 | 5/1999 | |
| WO | 01-97832 | 12/2001 | |
| WO | 2004-026320 | 4/2004 | |
| WO | 2006/078458 A1 | 7/2006 | |
| WO | WO2006/078458 * | 7/2006 | ............. A61K 31/73 |
| WO | 2009/037384 A1 | 3/2009 | |
| WO | 2009061607 A2 | 5/2009 | |

OTHER PUBLICATIONS

Dean Hainsworth, et al, Sustained Release Intravitreal Dexamethasone, 12 J Ocu. Pharmacol. Thera. 57 (1996).*
Marvin Myles, et al, Recent Progress in Ocular Drug Delivery for Posterior Segment Disease: Emphasis on Transscleral Iontophoresis, 57 Adv. Drug Del. Rev. 2063 (2005).*
MIGLYOL Product Information.*
International Search Report, dated Mar. 2, 2011, from corresponding application PCT/EP2010/067844.
Auriol et al., "Evaluation of Medium-chain Triglycerides as an Intraoocular Tamponading Agent in an Experimental Vitrectomy Model Rabbit", Presentation Abstract, Program 3766, Poster A232, May 2012.
Degussa, Creating Essentials, Tegosoft CT, "Cosmetic ester with properties similar to natural triglycerides but with a pleasant skin feel", Goldschmidt Personal Care, Aug. 2012, pp. 1-4.
Jonas et al., "Intravitreal Injection of Crystalline Cortisone as Adjunctive Treatment of Proliferative Diabetic Retinopathy", American Journal of Ophthalmology, vol. 131, No. 3, Apr. 2001, pp. 468-471.
U.S. Pharmacopeia, "Medium-Chain triglycerides", Pharmacopoeia Testing, glass-ts.com/pharmacopoeia, USP, BP, EP, JP glass testing Expert analysis for pharmaceuticals, Aug. 2013, pp. 1-4.
ST-Onge, et al., "Weight-loss diet that includes consumption of medium-chain triacylglycerol oil leads to a greater rate of weight and fat mass loss than does olive oil," Am. J. Clin. Nutr., Mar. 2008, vol. 87, No. 3, pp. 621-626.

* cited by examiner

*Primary Examiner* — Sean Basquill
(74) *Attorney, Agent, or Firm* — Young & Thompson

(57) ABSTRACT

A composition includes at least one fatty acid glycerol ester for use during or after a vitrectomy procedure, the composition being bioresorbable, being injectable in the vitreous cavity, having a density below 1, more preferably between 0.90 and 1, or a density above 1, more preferably between 1 and 1.5; having a surface tension of less than 50 dynes/cm more preferably ranging from 20 and 30 dynes/cm, being not susceptible to emulsify into droplets when injected; method for treating a retinal disorder involving the use of the composition.

17 Claims, No Drawings

METHOD FOR TREATING RETINAL CONDITIONS USING AN INTRAOCULAR TAMPONADE

FIELD OF INVENTION

The present invention relates to the field of the treatment of eye disorders, and to ophthalmic compositions, especially for use within the vitreous cavity of the eye.

More specifically, this invention relates to a solution and to a method using said solution in the treatment of retinal detachment.

BACKGROUND

The retina is the light-sensitive layer of tissue that lines the inside of the eye and sends visual messages through the optic nerve to the brain. The center of the retina is called the macula and is the only part capable of fine detailed vision.

Due to several causes such as cataract surgery, posterior vitreous detachment, diabetic proliferative retinopathy or trauma, the retina can become separated from its underlying layer of support tissues. When the retina detaches, it is lifted or pulled from its normal position and is removed from its blood supply and source of nutrition.

Initial detachment may be localized, but if untreated, the entire retina may become detached. The retina will degenerate and loose its ability to function if it remains detached. Central vision will be lost if the macula remains detached. If not appropriately treated, retinal detachment may thus cause permanent vision loss and lead to blindness.

The causes of retinal detachment can be divided into three main categories: (1) Rhegmatogenous retinal detachment, due to a retinal break or tear which allows the vitreous liquid to pass through the break and lift off the retina (2) exudative retinal detachment, due to leakage of fluid from under the retina and (3) traction retinal detachments: This type of detachment is due to pulling on the retina usually from fibro-vascular tissue within the vitreous cavity; proliferative diabetic retinopathy and proliferative vitreoretinopathy (scar tissue developing in association wit a rhegmatogenous retinal detachment) are the most common causes of tractional retinal detachment.

Vitrectomy is a surgical procedure consisting of the mechanical removal of vitreous liquid by the mechanical cutting and aspiration of the vitreous humour through a surgical instrument called a vitrector.

Vitrectomy may be used in the following clinical situations: (1) retinal detachment (2) complications or bleeding from diabetic eye disease (3) clouding of the vitreous jelly from one of many causes including blood, inflammatory debris or infection (4) macular hole (5) epiretinal membrane (6) a foreign body which has entered or passed through the eye and (7) intraocular infections (endophthalmitis).

Vitrectomy followed by injection of a retinal tamponade is a common technique used to repair retinal detachments. Retinal tamponade is achieved by either air, gas or silicone oil. Air and gas are temporary tamponades that last anywhere from days (air) to weeks depending upon the type of gas used (typically SF6 or C3F8). Silicone oil is used to achieve a permanent tamponade until the oil is surgically removed. The choice of tamponade is determined by the pathology, with longer tamponades (C3F8 or silicone oil) employed for more complicated cases such as tractional retinal detachment. Gas resorbs spontaneously based on its physicochemical properties, but silicone oil is removed when and if the retina is felt to be healed and stable. After healing, the oil tamponade is withdrawn by aspiration and replaced by a specific balanced salt solution, which is then replaced by fluid produced by the eye. Silicone oil removal can be tedious, and often is incomplete, with residual oil being unremoved due to small droplets or emulsified oil being caught behind or underneath tissues such as the iris or lens capsule. The residual oil usually causes problems such as persistent floaters or glaucoma (elevated intraocular pressure).

Tamponades may be characterized by two main physicochemical properties. The first property is the tamponing power; this property is given by a high surface tension of the solution; it allows the liquid to close the breaks in the retina and avoids leaking of the tamponade into the sub-retinal space. The second property is the force of reapplication; this property is given by a high difference of density between the tamponade and the vitreous fluid; this property is used to restore the retina to its initial place and to move the sub-retinal fluid out of the sub-retinal space created by the detachment.

The use of intraocular gases (usually either perfluoropropane (C3F8) or sulfur hexafluoride (SF6) or air) may be useful for flattening a detached retina or tamponading a macular hole and allowing an adhesion to form between the retina and its supporting tissues. These tissues need to be in apposition for a period of time, typically days to weeks, for this to occur. It is frequently necessary to maintain a certain head position following surgery when gas is used (see Macular Hole page). Vision in a gas filled eye is usually rather poor until at least 50% of the gas is absorbed. Possible complications of intraocular gas include progression of cataracts and elevated eye pressure (glaucoma). It is unsafe to fly in a plane or travel to high altitude while gas remains in the eye. The gas resorbs prior to adequate healing, and repeated injections are necessary.

The use of silicone oil is occasionally necessary instead of gas to keep the retina attached postoperatively. Different silicone oils may be used. Some of these oils have a density of below 1 to treat the retinal detachment of the upper part of the retina and some oils have a high density for treating the detachment of the lower part. Their surface tension is not very high but they have densities that provide a good force of reapplication. However, silicone oils may emulsify in the vitreous cavity resulting in a haze in the visual field. Also, when withdrawn, there are always small droplets that remain in the vitreous cavity inducing long term toxicity and visual problems due to the bubbles. If some silicone oil passes in the anterior chamber, it can lead to a difficulty to treat glaucoma. Inflammations of the posterior segment can be observed with these oils. Silicone remains in the eye until it is removed (necessitating a second surgery at a later date). Like gas, silicone oil can promote cataracts, cause glaucoma, and may damage the cornea. Silicone oil may lead to inflammation, which may participate to reproliferation of scar tissue (proliferative vitreoretinopathy) and recurrent tractional detachment. Furthermore, retinal detachment and vitrectomy can be associated with other conditions such as inflammation, proliferative symptoms, infections etc. The tamponade actually used are not associated with active substances able to treat or prevent these conditions.

To avoid these drawbacks, several attempts have been made.

A polymer gel has been developed (WO 99/21512) as tamponade. This is a photodymanic polymer which will gel when exposed to light and push back the retina. However, there is concern regarding toxicity issues due to the photodynamic ingredients of this gel.

WO 2006/078458 describes the use of a hydrogel of hyaluronic acid made with deuterium water. In this patent application, tamponade with increased density, in comparison to water, by addition of deuterium water and hyaluronic acid is attempted.

A recent patent (WO 2009/037384) uses a plastic bag placed in the vitreous cavity to be filled with the silicone oils. This strategy should avoid remaining oil after withdrawal. However, this procedure necessitates a second surgery to withdraw the bag at the end of the treatment.

TECHNICAL ISSUE

It is an object of the present invention to address one or more drawbacks associated with the prior art compositions. The main object of the present invention is to provide a tamponade solution having (1) a high tamponing power and (2) a high reapplication force, (3) the faculty to enhance healing of the retina, (4) which is not toxic even after long term exposure and (5) when the solution is removed, by aspiration after treatment, the remaining solution bioresorbs spontaneously.

DESCRIPTION OF THE INVENTION

The Applicant hereby proposes a composition comprising at least one fatty acid glycerol ester (FAGE) for use after a vitrectomy procedure, in order to restore the retina, said composition being bioresorbable, being injectable in the vitreous cavity, having a density below 1, preferably comprised between 0.90 and less than 1, more preferably ranging from 0.94 and 0.95 or a density above 1, preferably comprised between 1 and 1.5; having a surface tension of less than 50 dynes/cm more preferably between 20 and 50 dynes/cm, more preferably between 25 and 30 dynes/cm. Preferably, the composition of the invention is not susceptible to emulsify into droplets when injected in the vitreous cavity, as evidenced by the in-vitro test of example 3 below.

The composition of the invention is for use for replacing the vitreous humour, ordinarily present in the vitreous cavity and substantially or totally removed by vitrectomy. By substantially is meant that at least 90% v/v of the vitreous humour is removed.

In a vitrectomy, the whole content in vitreous humour is usually removed and the vitreous cavity is emptied. It may happen that part (i.e. less than 10% v/v of the initial volume of the vitreous humour) of the vitreous humour may remain within the cavity. In such event, the composition of this invention behaves as if the cavity was empty, i.e. it does not break into droplet, it does not emulsify and does not blur the vision of the patient. This ability of remaining homogeneous may be linked to the very nature of the fatty acid glycerol ester used according to the invention. Without willing to be linked by a theory, the Applicant may think that fatty acid glycerol ester provide a composition which is a continuous phase filling the vitreous cavity. This phase remains a continuous phase because of the surface tension of the fatty acid glycerol ester. This theory also relies on the observation that, in absence of surfactants, the composition of the invention remains in the form of a continuous, not breakable, phase. In an embodiment, the composition of the invention shall not include any droplets of possibly surrounding water in an environment where the ratio FAGE/water is of 90/10, as the surface tension is so high that the composition forms a bubble which cannot be broken or invaded by surrounding water or vitreous humour.

Preferably, the FAGE include glycerol fatty acid ester, glycerol acetic acid fatty acid ester, glycerol lactic acid fatty acid ester, glycerol citric acid fatty acid ester, glycerol succinic acid fatty acid ester, glycerol diacetyl tartaric acid fatty acid ester, glycerol acetic acid ester, polyglycerol fatty acid ester, and polyglycerol condensed ricinoleic acid ester, as long as they are colorless.

Preferred colorless FAGE are those having a surface tension of less than 50 dynes/cm more preferably between 20 and 50 dynes/cm, more preferably between 25 and 30 dynes/cm, as measured by the De Nouy technique using a K100SF Krüss tensiometer.

According to the invention, the composition of the invention is transparent, colorless, and allows a perfect reception of the light by the retina and the photoreceptors, avoiding any diffraction of the light, any trouble of the vitreous body content, and any loss of homogeneity of said content. Especially, the composition is free of any opacifying or coloring agents, especially free of contrast agents.

According to another embodiment, the oil can be colored with a lipophilic coloring agent to help the physician visualize the oil in the vitreous.

According to a preferred embodiment, the dynamic viscosity of the composition of the invention ranges from 20 and 60 mPa·s at a temperature of 20° C., preferably 25 to 55 mPa·s at a temperature of 20° C., more preferably 27 to 33 mPa·s at a temperature of 20° C. According to the invention, the term viscosity refers to capillary viscosity measured a 20° C.+/−0.1° C. The method for measuring viscosity is as described in the European Pharmacopeia, 5.0, 2.2.9. The determination of viscosity using a suitable capillary viscometer, such as for example Fischer scientific Capillaire Cannon-Fenske "reverse flow" standard ISO/DIN 3105, ASTM D2515, 445-446; Gamme 0.5-2 mm$^2$/s, volume 12 ml, length 295 mm.

According to a preferred embodiment, the refractive index of the composition of the invention ranges from 1.40 and 1.50 more preferably from 1.44 to 1.46 and even more preferably from 1.449 to 1.451.

According to another preferred embodiment, the composition forms in vivo a non water-miscible liquid phase in the form of a bubble, said liquid being in contact with the detached retina.

According to a preferred embodiment, the composition of the invention includes a fatty acid glycerol ester of natural origin which is devoid of any short term or long term toxicity and furthermore possesses healing up intrinsic properties.

Preferably, the present composition does not include organic solvents, silicone and perfluorocarbon oils or other non-bioresorbable vehicles.

The fatty acid glycerol esters used in the composition of the invention are such that the esters linked to the glycerol molecule preferably are carbon chains of a length of 6 to 20 carbons hereinafter referred to as C6-C20.

In an embodiment, the fatty acid glycerol esters used in the composition of the invention may be vegetable oils such as olive, corn, peanut, castor, sawflower, soya oils and hemisynthetic fatty acid glycerol esters.

In another embodiment, the composition of the invention does not contain any oil selected from the group consisting of olive oil, castor oil, saw flower oil and long chain triglycerides.

As a majority of retinal detachments affect the superior part of the retina, according to a preferred embodiment, the fatty acid glycerol esters of the composition of the invention are selected among triglycerides of density below 1. In this embodiment, preferred fatty acid glycerol esters are for example glyceryltricaprylate/caprate, medium chain triglycerides (MCT), long chain triglycerides, glyceryltricaprylate, glyceryltriundecanoate, glyceryl triacetate, or glyceryltricaprylate; structured glycerol esters such as for example glyceryltricaprylate/caprate/laurate or glyceryltricaprylate/caprate/linoleate; polyglycerol esters such as for example hexaglycerol esters of mixed fatty acid, or a combination or a mixture thereof. Among fatty acid glycerol esters, medium chain triglycerides are preferred.

According to an embodiment, in order to treat retinal detachment of the lower part of the retina, the fatty acid glycerol esters preferably has a density above 1, which may be due for example to chemical modification of said fatty acid glycerol esters. Preferred modified fatty acid glycerol esters are fluorinated or iodied fatty acid glycerol esters derivatives such as for example highly fluorinated fatty acid esters of glycerol or highly iodied fatty acid esters of glycerol; highly preferred are glycerol tripalmitate-F39 and/or glycerol tricaprate-I.

According to an embodiment, the composition of the invention contains two or three fatty acid glycerol esters such as a combination of medium chain triglycerides and glyceryltriundecanoate.

The fatty acid glycerol esters may be natural or hemisynthetic. A very preferred fatty acid glycerol ester is hemisynthetic medium chain triglycerides (MCT). The Applicant noticed that surprisingly, even with a surface tension of 20 to 30 dynes/cm, MCT does not disperse nor emulsify when injected in the vitreous cavity due to its high lipophilicity. The term "lipophilicity" refers to the ability of a chemical compound to dissolve in fats, oils, lipids, and non-polar solvents such as hexane or toluene. Preferably, the term liphophilic refers to composition having a solubility in oils superior to 0.01% w/w. The composition forms in vivo a bubble in contact with the detached retina. Furthermore, the density (0.94) of that triglyceride gives a significant power of reapplication to restore the retina (more potent than silicone oils); its bioresorbability is a main advantage compared to these silicones oils. Compared to the gas tamponade the time of tamponing is much longer as the fatty acid glycerol esters resorb in several months.

According to an embodiment, the composition of the invention is a solution. According to a preferred embodiment, the composition of the invention is not an emulsion. According to a preferred embodiment the composition of the invention does not include any polymer.

According to an embodiment, the composition of the invention is sterile. According to a preferred embodiment, the composition of the invention is sterilized by heat or filtrated. According to an embodiment, the composition is apyrogen.

According to an embodiment, the fatty acid glycerol ester can be injected after, before or in combination with other tamponades such as gases or silicone and perfluorocarbon oils.

According to an embodiment, the composition of the invention may comprise at least one lipophilic therapeutic agent and at least one bioresorbable fully saturated fatty acid glycerol ester, preferably a non-water miscible C6-C20 glycerol ester, wherein the composition is a solution comprising at least 90% w/w of C6-C12 fatty acid glycerol ester, in weight to the weight of total composition, a therapeutic agent in an amount of about 0 to 6% w/w, preferably more than 0 to 5.9% w/w, even more preferably from 0.05 to 5% w/w and still more preferably 0.5 to 2% w/w, in weight to the weight of total composition, the therapeutic agent being dissolved in the fatty acid glycerol ester.

Most generally, any compounds and compositions that are useful in treating, preventing, inhibiting, delaying the onset of, or causing the regression of the diseases and conditions related to the back of the eye may be therapeutic agents for use in the compositions of the invention.

In the meaning of this invention, the term "therapeutic agent" also includes analogs, prodrugs, salts and lipophilic esters of active therapeutic agents.

In a first embodiment, the therapeutic agent may be a healing enhancer, an anti-inflammatory agent, including, but not limited to a nonsteroidal anti-inflammatory agent or a steroidal anti-inflammatory, an endogenous cytokine, an agent that influences basement membrane, an agent that influences the growth of endothelial cells, an adrenergic agonist or blocker, a cholinergic agonist or blocker, an aldose reductase inhibitor, an analgesic, an anaesthetic agent, an antiallergic agent, an antibacterial agent, an antihypertensive agent, an immunosuppressor, an antiprotozoal agent, an antiviral agent, an antifungal agent, an anti-infective agent, an antitumor agent, an antimetabolite, a neuroprotective agent and/or an antiangiogenic agent; and analogs, prodrugs, salts and lipophilic esters thereof.

In a second embodiment, the therapeutic agent may be a healing agent including but not limited to vitamin A, vitamin E, vitamin D and vitamin K, alpha-tocopherol derivatives, retinol derivatives, lutein, aloe vera extracts such as aloine, omega-3 fatty acids, cyanocobalamin, L-cystine, pyridoxine, acetylcysteine, essential oils such as oil of calendula, cedar, lavender and their analogs and derivatives.

In a third embodiment, the therapeutic agent may be, steroidal therapeutic agent including but not limited to beclomethasone, betamethasone, corticosterone, cortisone, dexamethasone, dexamethasone palmitate, difluprednate, flumethasone, fluocinoloneacetonide, prednisolone, prednisone, rimexolone, tixocortol, triamcinolone and analogs, prodrugs, salts and lipophilic esters thereof; cell transport/mobility impending agents such as colchicine, vincristine, neuroprotectants such as nimodipine, brimonidine and related compounds; antibiotics such as chloramphenicol, ciprofloxacin, gentamycin, erythromycin, vancomycine, imipeneme, sulfadiazine; antifungals such as amphotericin B, ketoconazole, econazole, fluconazole, iconazole; antivirals such as idoxuridine, acyclovir, ganciclovir, cidofovir, interferon, DDI, AZT, foscarnet, vidarabine; anti-angiogenics such as TNP 470, medroxyprogesterone, thienopyridine SR 25289, thalidomide, sorafenib, sunitinib, pegaptanib, ranibizumab and bevacizumab, bevasiranib; non-steroidal antiinflammatories such as salicylate, indomethacin, ibuprofen, diclofenac, flurbiprofen, piroxicam; antineoplastics such as carmustine, cisplatin, bleomycin, carboplatin, carmustine, chlorambucil, cyclophosphamide, cytarabine, dacarbazine, dactinomycin, daunorubicin, doxorubicin, paclitaxel, fluorouracil (5-FU); immunosuppressors such as sirolimus, tacrolimus, cyclosporine A, azathioprin and analogs, prodrugs, salts and lipophilic esters thereof.

Preferred other therapeutic agents are anti-angiogenics such as TNP 470, medroxyprogesterone, thalidomide, pegaptanib, ranibizumab and bevacizumab, immunosuppressors such as sirolimus, tacrolimus and cyclosporine A; neuroprotectors such as nimodipine and brimonidine; antifungals, amphotericin B, miconazole, econazole; antiproliferatives fluorouracil (5-FU) and paclitaxel; anti-virals such as acyclovir, gancyclovir and nonsteroidal anti-inflammatories such as flurbiprofen and analogs, prodrugs, salts and lipophilic esters thereof.

Most preferred therapeutic agents are cyclosporine A, brimonidine, amphotericin B, miconazole, acyclovir and gancyclovir, 5-FU, paclitaxel, dexamethasone, dexamethasone palmitate, sirolimus, tacrolimus; and analogs, prodrugs, salts and lipophilic esters thereof. According to an embodiment of the invention, the therapeutic agent is a prodrug of one of the above-mentioned therapeutic agents. According to a further embodiment of the invention, the prodrug is a lipophilic ester of these above-mentioned therapeutic agents. More preferred are palmitate, myristate, laurate, caprate, caprylate, caproate, valerate, butyrate, propionate and acetate.

Most preferred healing agents are vitamins A, D, E and K, lutein, aloe vera extract such as aloine, cyanocobalamine.

According to an embodiment, the therapeutic agent included in the composition of the invention has a log P higher than 1 more preferably higher than 2.

According to an embodiment, the composition of the invention may include a combination of two or more therapeutic substance. Preferred combinations comprise an anti-inflammatory and an anti-angiogenic; an anti-inflammatory and a neuroprotective; an anti-inflammatory and an antifungal or an antibiotic, anti-inflammatory and healing agent.

According to an embodiment, the therapeutic substance is dissolved into a fully saturated glycerol ester with esters having carbon chains of 6, 7, 8, 9, 10, 12, 14, 16, 18 and/or 20 carbon atoms.

Another object of this invention is a method for treating retinal disorders, especially retinal detachment, related symptoms and causes, comprising injecting from 0.1 ml to 10 ml, preferably from 0.5 ml to 8 ml more preferably from 1 to 4 ml of the composition of the invention in the vitreous cavity, during or after a vitrectomy procedure preferably with a 27 or 30 gauge needle, said composition comprising at least one fatty acid glycerol ester, being bioresorbable, and having a surface tension of less than 50 dynes/cm more preferably ranging from 20 and 30 dynes/cm. In an embodiment, the composition comprises at least one lipophilic therapeutic agent and at least one bioresorbable fatty acid glycerol ester, preferably a non-water miscible C6-C20 glycerol ester, wherein the composition is a solution comprising at least 90% w/w of C6-C20 glycerol ester, in weight to the weight of total composition, a therapeutic agent in an amount of more than 0 to 5.9% w/w, in weight to the weight of total composition, the therapeutic agent being dissolved in the fatty acid glycerol ester. In an embodiment, the method according to the invention includes removing the vitreous fluid prior to injection of the composition of the invention in the vitreous cavity.

According to an embodiment, the concentration of the active substance in the composition of the invention may range from 0 to 6% w/w. For example, the tamponade can be injected pure without any additive but can be injected with 1% of paclitaxel dissolved.

Using 27 or 30 gauge needles is advantageous as it limits the damages caused by a bigger needle of 25 gauge which is usually used for highly viscous liquid such as silicone oils.

According to the method of the invention, vitreous cavity may be fully filled or partially with at least 1% to 100% of the cavity filled with the composition of the invention, during or after a vitrectomy.

According to the method of the invention, if only a part of the composition of the invention is removed from the vitreous cavity, the remaining composition bioresorbs spontaneously within a few weeks to few months.

Another object of the invention is a process for manufacturing the composition of the invention including a therapeutic agent in this embodiment, the manufacturing process consists in direct solubilisation of the active agent in the composition of the invention under stirring and eventually a heating of 25° C. to 50° C.

ADVANTAGES

Properties

The new solution does not disperse or leek into the sub-retinal space, it does not disperse nor emulsify in the vitreous cavity.

The new solution when injected in situ, i.e. in the vitreous cavity, will push back the retina, restore and close the retinal detachment.

Furthermore, the remaining droplets after withdrawal of the composition of the invention are bioresorbable.

The composition in the invention does not dissipate like gases.

Another advantage of solution of fatty acid glycerol ester is that, in an embodiment, it is transparent and colorless so that the surgeon can observe the healing of the retina through the filling of the vitreous cavity. A further advantage of the transparency is that it enables the patient to keep a slight vision during the procedure treatment until the withdrawal, if necessary, of the composition of the invention.

The refractive index of the glycerol esters is significantly different from that of water, helping the surgeon to visualize the tamponade, giving visible contour to the injected liquid.

DEFINITIONS

"Tamponade" is a liquid injected in the vitreous cavity to treat retinal conditions, especially retinal detachment.

"Tamponing power" is the ability of the tamponade fluid to close retinal dehiscences and prevent it from penetrating beneath the retinal tissue. This property is linked to its interfacial and surface tension.

"Force of reapplication" is the ability of the tamponade fluid to restore the retina to its proper anatomic location. This property is linked to the density of the fluid which ensures it exerts significant pressure on the retina.

"lipophilic": Lipophilicity refers to the ability of a chemical compound to dissolve in fats, oils, lipids, and non-polar solvents;

A "bioresorbable" compound is a compound that progressively disappears in a biologic environment;

"Fatty acid glycerol ester" is a molecule of glycerol which is esterified by three fatty acids. It is also called triglyceride.

"MCT" means triglyceride wherein the carbohydrate chain has 8 to 12 carbon atoms;

"injectable" means able to be administered through injection;

"endotoxine" means glycolipids and their metabolites found in the outer membrane of gram-negative bacteria. Endotoxine may be assayed, for example, using a Limulus Amoebocyte Lysate (LAL) test kit (Pyrogent Plus N284);

"about" means approximately or nearly, and when applied to a value or a range, plus or minus 10% of the numerical value or range;

"vitreous" means the vitreous or vitreal cavity of the eye, also called corpus vitreum; "treatment" means reversal, alleviation, inhibition, prevention, stabilization, prophylaxis, relief or cure of an ocular condition.

EXAMPLES

Example 1

Compositions of the Invention

| Composition | Components |
|---|---|
| 1 | MCT 99% |
|   | Vitamin E 1% |
| 2 | MCT 99.5% |
|   | Dexamethasone palmitate 0.5% |
| 3 | MCT 95% |
|   | glyceryltricaprylate/caprate/linoleate 5% |
| 4 | Castor oil 98% |
|   | Aloine 2% |
| 5 | MCT 50% |
|   | Olive oil 49.5% |
|   | Paclitaxel 0.5% |
| 6 | MCT 100% |
| 7 | Fluorinated MCT 100% |
| 8 | Fluorinated MCT 98% |
|   | 5-FU 2% |
| 9 | Iodied MCT 100% |

Example 2

Comparison of Physico-Chemical Properties of MCT with Usual Tamponade

TABLE 1

| Physico-chemical properties | | | | |
|---|---|---|---|---|
| Physico-chemical properties | Air | Perfluoro-carbon gas | Silicone oils | MCT |
| Density | ≈0 | 2 | 0.97 | 0.94-0.95 |
| Surface tension (dynes/cm) | 73 | 54 | 40 | <30 |
| Viscosity (mPa · s) | ≈0 | 1.4-2.8 | 1000-5000 | 27-33 |
| Refractive index | 1 | 1.27-1.33 | 1.404 | 1.449-1.451 |

Example 3

Evaluation of the Non-Emulsifying Property of the Compositions of the Invention

In Vitro Evaluation

It is hereby considered that any composition passing the following test is not capable to emulsify when or after intravitreal injection. Two millilitres of anyone of compositions 1-8 are placed in a vial with 2 ml of water. The vial is placed on a vortex agitator (model TOP-MIX by Fisher Scientific) at speed 500 rounds per minute to mimic the movements of the head. A visual observation is made to check whether or not the composition is dispersed in fine oil droplets.

Results: none of compositions 1-9 emulsifies and each composition remains as a unique oil volume (bubble).

In Vivo Evaluation

In vivo evaluation was performed to confirm the efficacy of the above-described in-vitro test. The result of the in-vivo evaluation evidenced that the in-vitro test is sufficient for assessing whether or not a composition may or may not emulsify in vivo, when or after injection in the vitreous body.

Protocol

30 New Zealand white rabbits from 2 to 2.5 kg were be operated under general anesthesia with Ketalar (50 mg). Posterior vitrectomy by a surgical approach was performed on the rabbit's eye. A lens of Kilp was used to visualize the fundus of the eye during vitrectomy.

After the vitrectomy, the compositions 1-9 are injected using a 23 gauge needle so as to fill the vitreous cavity.

24 eyes receive compositions 1-9 and the fellow eye of each rabbit operated serving as a witness.

6 eyes receive a standard silicone oil of 1300 cts after posterior vitrectomy fellow eye used as control.

The rabbits:
are submitted to a direct examination the anterior segment and fundus in binocular indirect ophthalmoscope at J7, J30, J60, J90.
are sought from an inflammatory reaction in the anterior chamber graded 0, 1 (fibrinous reaction with no lumps or clumps of fibrin occupying an area less than or equal to one quadrant), 2 (cluster fibrin occupying an area between one and two quadrants), 3 (mass of fibrin occupying an area between two and three quadrants), 4 (cluster fibrin occupying the entire anterior chamber).
are sought emulsification of the composition of the invention by the presence of oil droplets in the anterior chamber grade 1a or 2a pseudohypopion grade.
are sought emulsification of the composition of the invention in the posterior chamber by the presence of oil droplets in the posterior (back) cavity
are sought emulsification of the composition of the invention possible prevention of the visualization of the fundus grade 1p or impeding the visualization of the fundus degree 2p. 0p grade due to emulsification of the product.

Results:

At no time oil droplets could be observed in the rabbit's eye. No indicia of emulsification were observed.

This experiment confirms that the composition of the invention does not emulsify spontaneously in the rabbit eye.

The invention claimed is:

1. A method for treating retinal disorders, comprising, injecting into the vitreous cavity of a subject in need thereof, during or after a vitrectomy procedure, a non-emulsified tamponade composition comprising at least 90% w/w of one or more C6-C20 fatty acid glycerol ester,
said tamponade composition having a surface tension of less than 50 dynes/cm, and a density of less than 1, and
said tamponade remaining non-emulsified while in the vitreous cavity,
wherein said retinal disorders are retinal detachment, break or tear; complications or bleeding from diabetic eye disease; clouding of vitreous jelly from one of many causes including blood, inflammatory debris or infection; macular hole; epiretinal membrane; consequences of entry or passing of a foreign body through an eye; or intraocular infections.

2. The method according to claim 1, wherein the composition has a density between 0.90 and less than 1.

3. The method according to claim 1, wherein the composition has a dynamic viscosity ranging from 20 to 60 mPa·s at a temperature of 20° C.

4. The method according to claim 1, wherein the composition has a refractive index ranging from 1.40 to 1.50.

5. The method according to claim 1, wherein the composition further comprises at least one lipophilic therapeutic agent.

6. The method according to claim 5, wherein the composition comprises the therapeutic agent in an amount of more than 0 to 5.9% w/w, in weight to the weight of total composition, the therapeutic agent being dissolved in the fatty acid glycerol ester.

7. The method according to claim 1, comprising at least 90% w/w of at least one C6-C12 fatty acid glycerol ester.

8. The method according to claim 1, comprising
removing the vitreous fluid of the subject prior to injecting the tamponade composition into the vitreous cavity, and
injecting from 0.1 ml to 10 ml of the tamponade composition into the vitreous cavity.

9. The method according to claim 1, wherein said tamponade composition has a surface tension of 20 to 30 dynes/cm.

10. The method according to claim 1, wherein the tamponade composition is injected into the vitreous cavity during a vitrectomy procedure.

11. The method according to claim 1, wherein the retinal disorder is a retinal detachment, break, tear or hole.

12. The method according to claim 1, wherein the tamponade composition comprises at least 95% of medium chain triglycerides.

13. The method according to claim 1, wherein the tamponade composition comprises at least 99% of medium chain triglycerides.

14. The method according to claim 1, wherein the tamponade composition comprises non-fluorinated fatty acid glycerol esters.

15. The method according to claim 1, wherein the tamponade composition comprises at least 90% w/w of one or more C6-C20 non-fluorinated fatty acid glycerol ester.

16. The method according to claim 1, wherein the tamponade composition comprises at least 98% w/w of one or more C6-C20 non-fluorinated fatty acid glycerol ester selected from medium chain triglycerides, castor oil and olive oil.

17. The method according to claim 8, wherein the tamponade composition is injected into the vitreous cavity with a 27 to 30 gauge needle.

* * * * *